(12) United States Patent
Huang et al.

(10) Patent No.: US 8,345,264 B2
(45) Date of Patent: Jan. 1, 2013

(54) LASER REFLECTION OPTICAL FIBER SENSOR

(75) Inventors: Haiying Huang, Arlington, TX (US); Uday Shankar Tata, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 938 days.

(21) Appl. No.: 12/152,451

(22) Filed: May 14, 2008

(65) Prior Publication Data

US 2009/0135427 A1 May 28, 2009

Related U.S. Application Data

(60) Provisional application No. 60/917,754, filed on May 14, 2007.

(51) Int. Cl.
*G01B 11/30* (2006.01)
*G01B 11/16* (2006.01)
*G01N 21/55* (2006.01)
*G01N 21/00* (2006.01)
*G02B 6/00* (2006.01)

(52) U.S. Cl. ....... 356/600; 356/32; 356/445; 356/237.2; 385/12

(58) Field of Classification Search .................. None
See application file for complete search history.

(56) References Cited

U.S. PATENT DOCUMENTS

| | | | | |
|---|---|---|---|---|
| 4,278,349 A | * | 7/1981 | Sander | 356/44 |
| 4,699,511 A | * | 10/1987 | Seaver | 356/136 |
| 5,065,630 A | * | 11/1991 | Hadcock et al. | 73/802 |
| 5,128,535 A | * | 7/1992 | Bock et al. | 250/227.21 |
| 5,367,583 A | * | 11/1994 | Sirkis | 385/12 |
| 6,913,079 B2 | * | 7/2005 | Tubel | 166/250.01 |
| 6,943,340 B2 | * | 9/2005 | Tubel et al. | 250/227.14 |
| 2006/0072888 A1 | * | 4/2006 | Lagakos et al. | 385/117 |
| 2006/0090574 A1 | * | 5/2006 | Moore et al. | 73/862.55 |

OTHER PUBLICATIONS

Chin, R. et al., "NIR-PRFS Fiber Optic Corrosion Sensor," (1996) SIPE, 2682:275-286.
Cooper, K.R., et al., "Optical Fiber-Based Corrosion Sensor Systems for Health Monitoring of Aging Aircraft," (2001) IEEE 37:947-856.
Dantan, N., et al., "Fiber optic pH sensor for early detection of danger of corrosion in steel-reinforced concrete structures," (20058) SPIE 5758:274-284.
Dong, S., et al., "Intensity-based optical fiber sensor for monitoring corrosion of aluminum alloys," (2005)Applied Optics 44(27):5773-5777.
Dong, S., et al., "Optical fiber long-period grating-based Cu2+ measurement," (2005) SPIE 5634:627-633.
Elster, J., et al., "Optical Fiber-Based Chemical Sensors for Detection of Corrosion Precursors and By-Product," (1998) SPIE 3540:251-257.
Greene, J.A., et al., "Grating-Based Optical Fiber-Based Corrosion Sensors," (1996) SPIE 2718:170-174.

(Continued)

*Primary Examiner* — Gordon Stock, Jr.
(74) *Attorney, Agent, or Firm* — Daniel J. Chalker; Edwin S. Flores; Chalker Flores, LLP

(57) ABSTRACT

A sensor, sensor assembly and a method of sensing, in which the sensor is in contact with a material or structure and the sensor directly measures one or more property changes in the material by means of light reflection and scattering using a reflective target.

18 Claims, 13 Drawing Sheets

OTHER PUBLICATIONS

Greene, J.A., et al., "Optical Fiber Corrosion Sensors for Aging Aircraft," (1998) SPIE 3399:28-33.

Himour, A., et al., "Optical-Fiber Corrosion Sensor Based on Deposit of Au/Ni-P," (2005) Japanese Journal of Applied Physics 44(9A):6709-6713.

Huang, H., et al., "A Novel All-Fiber Surface Roughness Sensor Based on Laser Scattering," (2007) The 6th International Workshop on Structural Health Monitoring, Stanford University, United States.

Kermis, H.R., et al., "Rapid method for the preparation of a robust optical pH sensor," (2003) The Analyst 128:1181-1186.

Li, X.M., et al., "Fiber Optic Corrosion Sensor Fabricated by Electrochemical Method," (1998) SPIE 3330:126-133.

Lo, Y., et al., "Development of Corrosion Sensors Using a Single-Pitch Bragg Grating Fiber with Temperature Compensations," (1998) SPIE 3325:64-72.

Qiao, G., et al., "Thin Fe-C Alloy Solid Film Based Fiber Optic Corrosion Sensor," (2006) Proceedings of the 1st IEEE International Conference on Nano/Micro Engineering and Molecular Systems Zhuhai, China.

Werner, T., et al., "Optical sensor for the pH 10-13 range using a new support material," (1993) Fresenius J Anal Chem 346:564-568.

Woodruff, M.W., et al., "Corrosion sensing of aluminum using optical fiber," (1994) SPIE 2191:511-515.

* cited by examiner

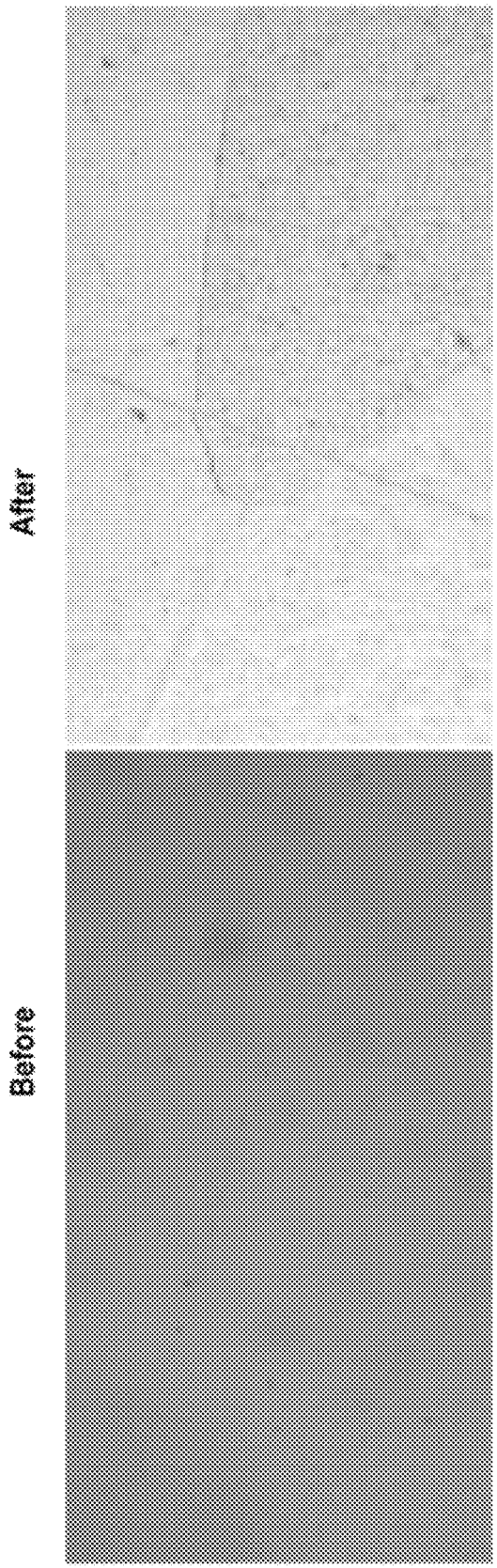

LASER REFLECTION OPTICAL FIBER SENSOR

CROSS REFERENCES TO RELATED APPLICATIONS

This application claims the benefit of U.S. Provisional Application No. 60/917,754 filed May 14, 2007.

STATEMENT OF FEDERALLY FUNDED RESEARCH

This invention was made with U.S. Government support under Contract No. N00014-06-1-1150 awarded by the U.S. Office of Naval Research and Contract No. FA9550-06-C-0064 awarded by the Air Force Office of Scientific Research. The government has certain rights in the invention.

BACKGROUND OF THE INVENTION

This invention relates in general to the field of sensors with reference to sensors relying on light scattering properties.

Measurements of materials and any change in their properties, such as fatigue deformations, strain, and corrosion, are necessary for routine or experimental assessment and monitoring of such materials as well as the equipment, machines, or subjects they reside in. Such measurements ensure structural safety and integrity among other things. Current tools for measuring these changes are either inadequate, too large, destructive, of low sensitivity or unreliable.

SUMMARY OF THE INVENTION

The invention described solves many problems associated with current limitations in measuring, assessing or monitoring material changes, such as fatigue deformations, strain, and corrosion.

Described herein are optical sensors and methods of assessing one or more properties of a structure or material, particularly a material surface by using said sensors. Light reflection/scattering via sensor assembly provides one means for a sensor described herein to measure, assess, monitor and/or detect a property changes to a material. Properties that may be measured, assessed, monitored and/or detected by a sensor described herein include strain, corrosion, temperature, fatigue, deformation, displacement, microstructure, acoustic wave, and combinations thereof.

In one or more embodiments the sensor described herein is a strain gauge. In other embodiments, the sensor is a corrosion sensor. In still other embodiments, the sensor is a temperature sensor. In additional embodiments, the sensor is a fatigue sensor. In further embodiments, the sensor is a deformation sensor. In still added embodiments, the sensor is a displacement sensor. In yet added embodiments, the sensor is a microstructure sensor. In still further embodiments, the sensor is an acoustic wave sensor. When desired, one or more of the sensor properties may be combined.

In one or more embodiments are provided an entire sensing unit that includes one or more of the following, such as an energy harvesting component, light source, sensor, optical power detector, and wireless transmitter.

Those skilled in the art will further appreciate the above-noted features and advantages of the invention together with other important aspects thereof upon reading the detailed description that follows and in conjunction with the drawings.

BRIEF DESCRIPTION OF THE DRAWINGS

For a more complete understanding of the present invention and the advantages thereof, reference is now made to a description, taken in connection with the accompanying figures, wherein:

FIGS. 12B and 12C depict optical images of samples from FIG. 15A before (B) and after (C) annealing;

DETAILED DESCRIPTION OF THE INVENTION

Figure 1A:
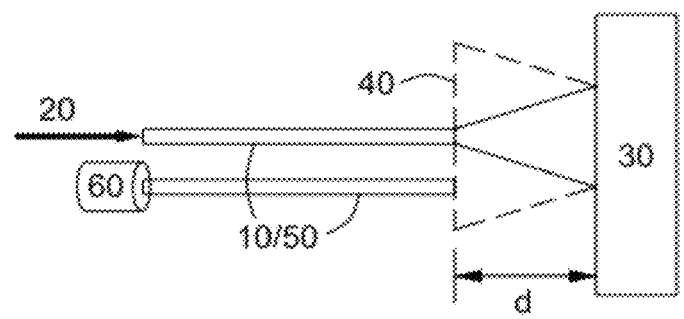
FIG. 1A and FIG. 1B each depict schematics of a sensor design.

Although making and using various embodiments are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

Strain measurement, corrosion and fatigue detection and changes in microstructure are among the properties necessary to ensure structural safety and integrity of a material or structure. Real-time monitoring and off-line inspection of a material, structure and the parts, machines or equipment it comprises are now in demand. Unfortunately, conventional strain gauges cannot sustain large cycles of fatigue loading. Corrosion detectors require very large equipment or offer only an indirect evaluation with a high false alarm rate. When optical fiber corrosion sensors are used most are transmission-type sensors that require access of the optical fiber from both ends. Those sensors that act as reflection-type optical fiber sensors use only indirect sensing mechanisms in which relationships are correlated (e.g., actual corrosion experienced by the structures is only correlated to a corrosion as measured by the sensors) and such correlations have proven to be difficult to interpret and/or monitor, hindering applications of corrosion sensors in real-time applications.

Described herein is an optical sensor and method of sensing material properties and/or conditions of a material and/or structure. An all-fiber sensor is provided that operates by advantageously using laser scattering from an illuminated target. A typical sensing component described includes at least two parallel fibers. A first fiber is an illumination fiber. A second fiber is a receiving fiber. The first fiber is coupled to a light source that delivers light to a target. The second fiber collects scattered light from the target. The target is a reflective material that scatters light. A preferred target does not absorb a lot of light; although, the target may comprise an absorbing material as long as the material also exhibits light scattering properties. In many instances, a metal material is used for the target.

The target may be of any shape, including circular or rectangular. And, while small, the target may a range of thicknesses, from only a few micrometers to a few millimeters. The general dimension of the target is guided by the application for which it is used.

A sensing component, generally comprising the optical fibers and target, itself as described herein is very small and may be about 100 mm or less and may be less than about 1 mm in diameter. A sensing component and its assembly may be cooperative with one or a number of structures and said materials. In one form, it may be provided in a confined space with or without additional optical fibers. It may further be cooperative with other equipment, hardware and/or software.

A sensor as described may be installed in a confined space with or without additional optical fibers that deliver light and transmit reflected light out. In one or more embodiments, a sensing unit or system will include one or more of the following, including an energy harvesting component, light source, sensor, optical power detector, and wireless transmitter.

Figure 1B:
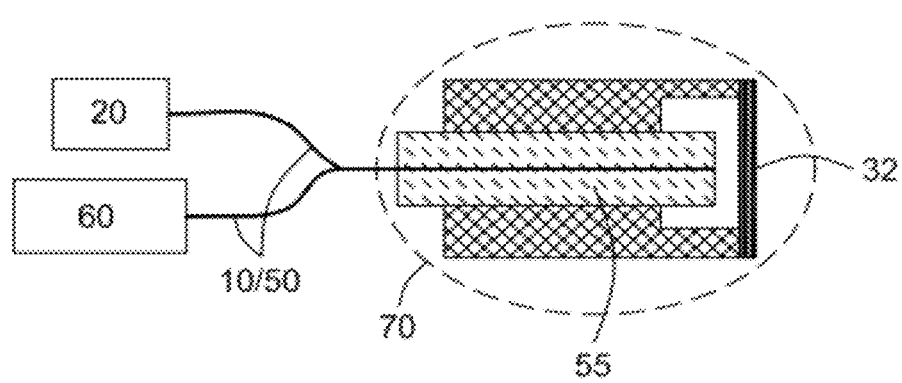
Figure 2A:
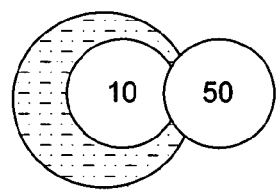
FIG. 2A depicts in schematic form light scattering of a smooth material surface.
Figure 2B:
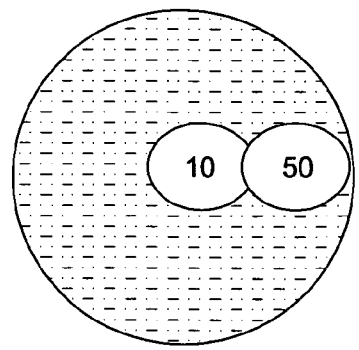
FIG. 2B depicts in schematic form lights scattering of a less smooth material surface.

FIGS. 1A and 1B are representative schematics of embodiments of sensor assemblies as described herein. In both, fiber 10 is an illumination fiber coupled to light source 20 that provides light to a target 30 (FIG. 1A) or 32 (FIG. 1B). FIG. 1A shows that a portion of reflecting light 40 from the target that typically forms a reflecting pattern is collected by a second fiber. In both FIGS. 1A and 1B, the second fiber is fiber 50 and via this fiber, light is identified/detected/recorded by detector 60. In FIG. 1A, the symbol d is the distance between target 30 and the end of fiber 50 nearest the target. The size of the reflecting pattern is influenced by both the distance d and the surface of the target. When a target surface is smooth, has little damage, or little corrosion, a small distance d has a small reflecting pattern as schematically illustrated in FIG. 2A. Increasing distance d will increase the size of the reflecting pattern of reflecting light 40, as schematically illustrated in FIG. 2B. For a fixed distance d, the light pattern of reflecting light 40 may be affected by the surface of the target. A small light pattern (FIG. 2A) is typical for certain properties, such as smooth microstructure, little damage, little corrosion. A larger light pattern (FIG. 2B) is typical for other properties of the target that scatters the reflecting light (e.g., rough microstructure, damage, corrosion).

Referring again to FIG. 1B, the figure shows another embodied optical detecting system described herein that includes a light source 20, two optical fibers 10/50, a sensor probe 55, a sacrificial component or film 32, and an optical power detector 60. The sensor probe and sacrificial component are packaged into a sensor head 70. The sensor head may be 1 mm or less or may be 10 mm or less, depending on application or desired configuration. A sacrificial component assists when sensing corrosion and fatigue. As such, a sacrificial component is preferably a material that has known corrosion characteristics or known fatigue characteristics. The target and/or sacrificial material may be the same material that is being tested, assessed, monitored and/or detected.

Figure 1C:
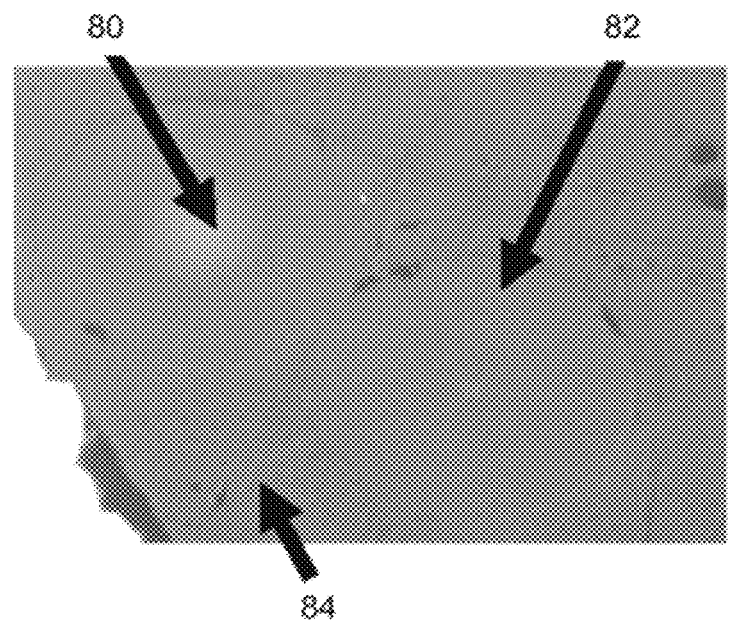
FIG. 1C depicts a representative sensor head as described herein.

A detailed view of one embodiment of a sensor head is shown in FIG. 1C, which shows the head constructed of two parallel fibers, first fiber 80 and second fiber 82, embedded using an embedding material 84, such as an epoxy. In the embodiment depicted in FIG. 1C (which is generally a front view of sensor probe 55 of FIG. 1B), first fiber 80 is a single mode fiber (SMF) and second fiber 82 is a multi-mode fiber (MMF), placed adjacent each other. A target or sacrificial component is positioned perpendicular to the fiber axis. The distance between the sensor probe and the target or sacrificial component is adjusted to be in the linear regions of a distance-intensity curve as described further below (and illustrated in FIGS. 4 and 14). The actual distance between the fibers and the target will depends on the application. Typically, the distance between said components may vary from about 0 mm to about 4 mm.

With a sensor head construction as described with FIG. 1B and FIG. 1C, in one example, a light source is coupled to a first fiber (e.g., SMF as described with FIG. 1C), which delivers light to the sacrificial film or target. After exiting the first fiber, light impinges on the sacrificial film (or target) and is reflected back to the sensor probe. Part of the reflected light is collected by the second fiber (e.g., MMF, as described with FIG. 1C). The amount of light reflected is influenced by the reflectivity of the sacrificial film and the sacrificial film or target will be altered when properties of the film are altered (e.g., corrosion, bending, fatigue, strain, microcracks, etc.). Accordingly, a decrease in light collected by the second fiber will occur when reflectivity of the sacrificial film or target is affected (e.g., by corrosion, bending, fatigue, strain, microcracks, etc.). As such, the optical power output of the sensor serves as an indicator for the development of property changes of the sacrificial film/target, and property changes of the sacrificial film/target are effected by the environment (e.g., corrosion, bending, fatigue, strain, microcracks, etc.).

As described herein, a sensor head is also packaged in such a way that only one side of the sacrificial film or target is exposed to such effects of the environment (e.g., corrosion, bending, fatigue, strain, microcracks, etc.), while the other side of the sacrificial film or target is finely polished and is isolated from such an environment. The sensitivity of the sensor is also determined by the thickness of the sacrificial film or target. Thus, one or more sensors with different thicknesses of the sacrificial film or target may be suitably employed to track progression and changes in the environment.

Figure 3A:
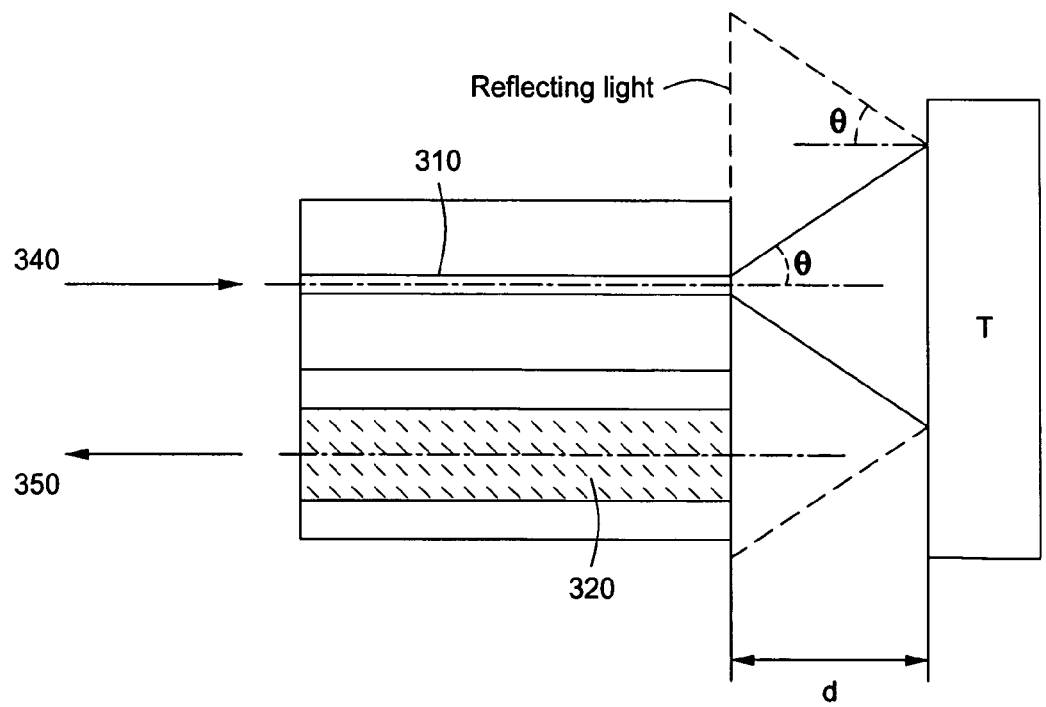
FIG. 3A depicts a schematic of a further sensor design.

In a simulation, a sensor comprising two fibers, 310 and 320, in parallel were provided normal to a target as depicted in FIG. 3A. The illumination fiber 310 was a single mode fiber. The receiving fiber 320 was a multi-mode fiber. Light was provided to the sensor by a laser diode 340. The target T was in contact with a motorized translation stage. Light scattering from the target (e.g., surface) was collected by receiving fiber 320 and delivered to an optical power meter 350 in operable communication with a computer to resolve light measurements, as depicted schematically in FIG. 3A. Optical power of the collected light scattering and position of the translation stage were acquired simultaneously. Intensity vs. distance between sample and sensor were plotted. A theoretical model of the light intensity collected was prepared based on the description below.

Sensing of a material and its properties using continuous light means that optical light confined in an optical fiber is based on total internal reflection. For single mode fiber (SMF), only one fundamental mode of the optical wave can propagate in the fiber. For multi-mode fiber (MMF), several fundamental modes may coexist and propagate. The intensity pattern of a SMF typically presents in a Gaussian profile. When optical light exits an illuminating fiber, it diverges at an angle θ that is defined as the numerical aperture of the fiber (FIG. 3A). The shape of the light beam may be visualized as a light cone with a diameter of a base that increases as it propagates away from the fiber. Impinging upon a target surface, optical light is reflected based on Snell's law, assuming a target surface is substantially and optically reflective or smooth. The wavefront remains as a circle and the diameter of the circle increases as the reflected optical wave propagates toward a receiving fiber. When the reflected light hits an end face of the receiving fiber, part of the light is coupled into the receiving fiber. To increase the amount of light collected by a receiving fiber, an MMF with a large core may be used (to increase signal-to-noise ratio). The amount of light that is coupled into the receiving fiber is based on the area of the reflected pattern overlap with the core area of the receiving fiber.

Figure 3B:
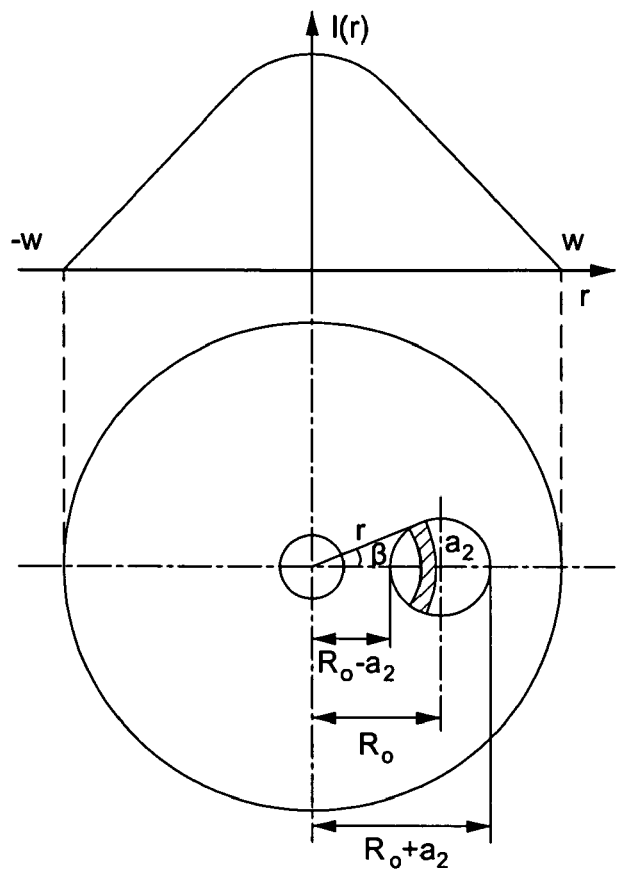
FIG. 3B depicts a schematic of a side view of two fibers of a sensor described herein.

A side view of a sensor design of FIG. 3A and the reflected light pattern is shown in FIG. 3B. Dashed lines indicates the boundary of light. The radius of the light w is calculated from the numerical aperture of the optical fiber, the core diameter of fiber 310 is $2a_1$, and the distance between the optical fiber and target is d.

Because $$I = \frac{I_o}{w^2} e^{\frac{-r^2}{w^2}}$$

where w is beam spot radius, r is radial distance and $I_o$ is maximum intensity (FIG. 3B), and $$dP = \int d\phi \int I r dr$$

then, theoretically, optical power (P) of a reflected light, collected by the receiving fiber, is a function of distance between optical fiber and the target, as shown in Equation 1, where d is distance and a is radius of the optical fiber core, $$P = \int_{d-a}^{d+a} \frac{2P_o}{\pi w^2} \cos^{-1}\left(\frac{r^2 + d^2 - a^2}{2rd}\right) r dr. \tag{1}$$

Figure 4:
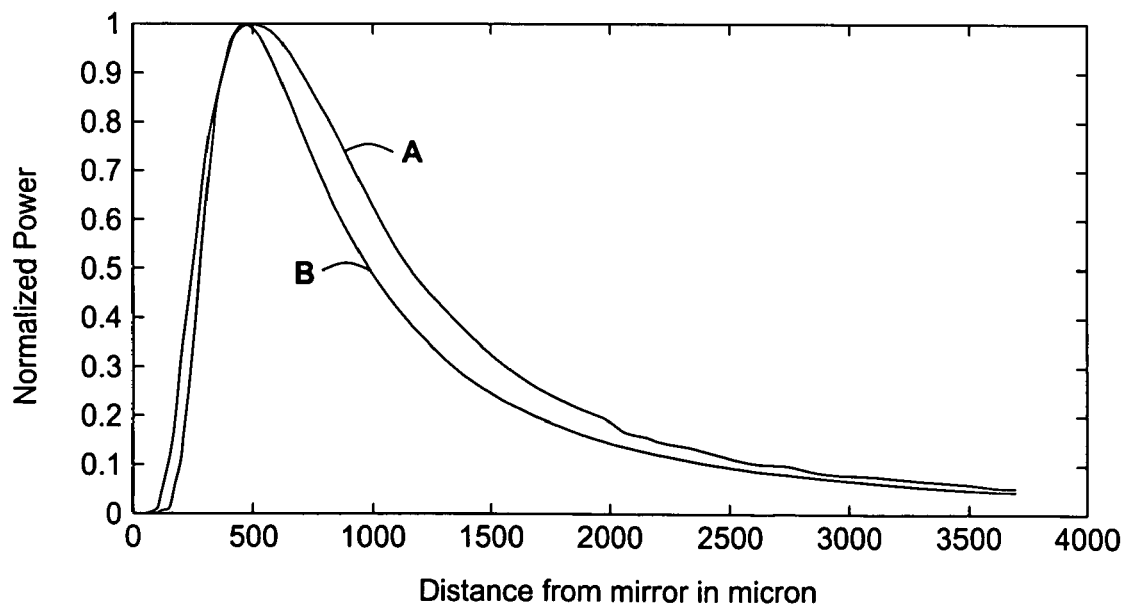
FIG. 4 depicts power of a sensor in a simulation as compared with a theoretical model.

From the simulation described, FIG. 4 was obtained, indicating a near perfect union of the distance-power relationship in sensor design practice (line A) and theory (line B). In the simulation, the target surface provided is smooth in order to achieve the near perfect relationship between intensity of collected light and distance.

Figure 5:
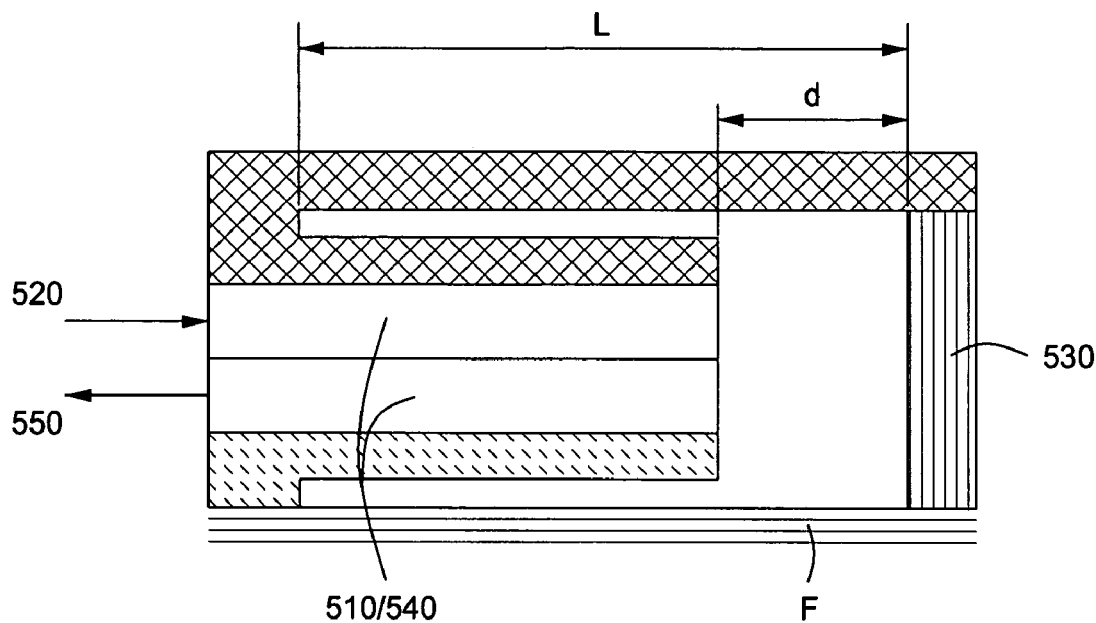
FIG. 5 depicts a schematic of a further sensor design.

In one or more embodiments, the sensor described is a fatigue sensor and strain sensor as depicted in FIG. 5. Such a sensor may also be a corrosion sensor. The novelty of a strain sensor described herein is that it may be further designed to sustain various fatigue loading conditions. A corrosion sensor described herein detects/assesses/monitors corrosion directly by monitoring light reflection from the surface of the target.

For sensing of fatigue/strain/corrosion, a first fiber 510 serves as an illumination fiber. The first fiber provides light from light source 520 to a surface 530 of a reflective target. A second fiber 540 collects light reflected from surface 530. Second fiber 540 is coupled with a receiver/detector 550 to gather reflected light. Receiver/detector 550 may further assess/measure/compute/evaluate optical power of the collected light. Fatigue, strain and/or corrosion are assessed/identified/detected by adjustments in optical power of the collected light.

Figure 7:
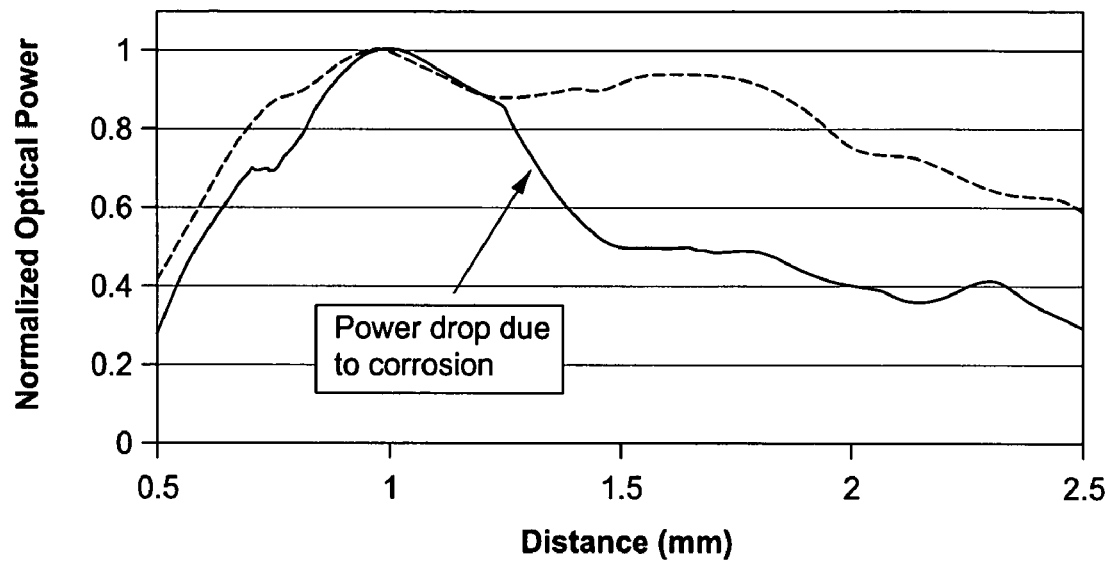
FIG. 7 depicts power versus distance of a sensor.

When sensing corrosion, the sensor is exposed to an environment considered/predicted to be corrosive. Because corrosion typically begins at an outer surface of a target and penetrates toward an inner surface/layer, pits or variations in the surface (e.g., depth) that develop on the target will alter reflected light and be detected by the sensor. Sensors with targets having variations in thickness may be advantageous and employed to monitor progression of corrosion. In one embodiment, prediction/identification/detection of corrosion uses the sensor configuration as described in FIG. 5. The surface of the target is the sensing element that is subject to a corrosive environment. A decrease in optical power of the reflected light is a positive indicator of corrosion (FIG. 7). When desired, severity of corrosion is quantified by having the surface of the target prepared with a specific thickness. In addition or as an alternative, several sensors directed to different surfaces (e.g., targets of varying thickness) may be used to monitor/detect/identify corrosion of a target and monitoring/detecting/identifying may be performed over time.

When sensing fatigue, a target is typically in contact with a second component that is loaded. The second component is a material with fatigue damage to be monitored/assessed/detected. Typically the loading employed is fatigue loading. Consequently, the target experiences similar loading to that of the second component or material for assessment. The sensor detects fatigue from, a change in microstructure (e.g., surface roughness); any changes of the target surface may then be correlated to the fatigue cycle that the second component has experienced.

When sensing strain, the sensor and target are rigidly in contact with/on a fatigue resistant material F. The fatigue resistant material F is further in contact with a second component, the second component being a material that is to undergo strain. Strain of the second component will induce a change in distance d between the target and the end of fiber 550 that, in turn, changes optical power of light collected by fiber 550.

Still referring to FIG. 5, optical power of reflected light collected by the fiber 540 is a function of the distance between the optical fiber and the surface of the target also referred to herein as cavity distance and denoted as d in FIG. 5. A relationship between optical power (P) of reflected light and cavity distance is calculated from an integration of reflected light entering the fiber 540 using d and a, as the radius of the optical fiber core, as provided in Equation 1.

Figure 6:
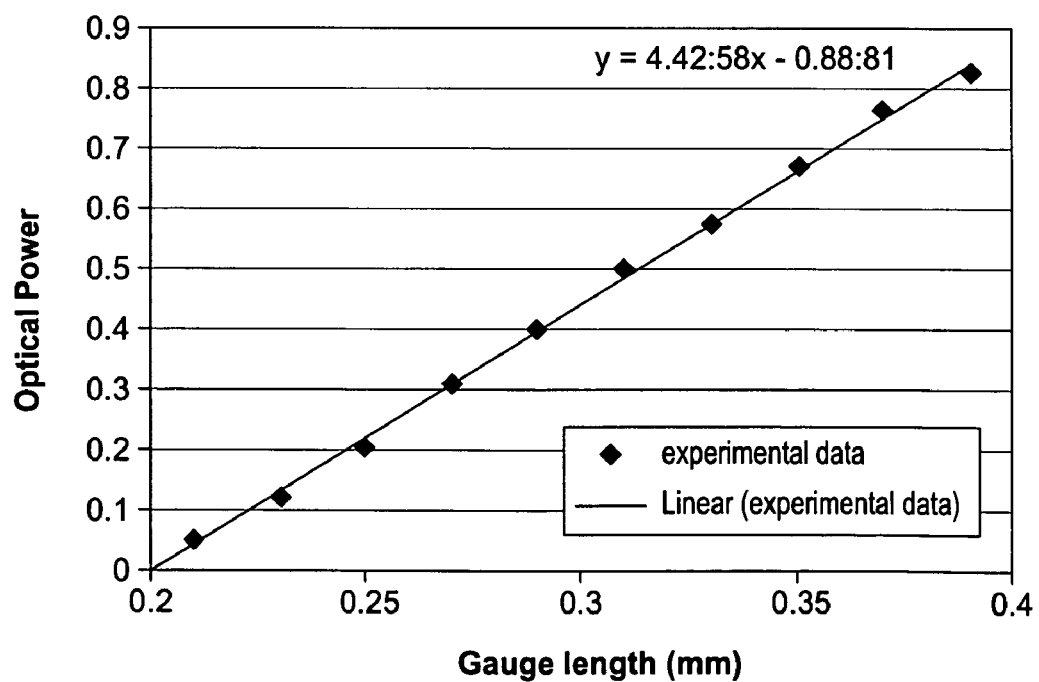
FIG. 6 depicts power versus gauge length of a sensor described herein.

The simulated distance-optical power relationship, as shown in FIG. 4, indicates a suitable distance range for d (cavity distance) of at least about 300 to 750 microns. In addition, at a cavity distance of about 350 microns, a relationship between gauge length L (as shown in FIG. 5) and reflected optical power appears linear, as further shown in FIG. 6. Therefore, change in cavity distance may be calculated from the measured optical power. The cavity distance change, Δd, is from elongation of the gauge length due to strain. Therefore, strain experienced by the gauge area may be calculated as $$\varepsilon = \frac{\Delta d}{L_0},$$

where $L_0$ is the initial gauge length.

Assuming a fixed resolution in distance measurement for sensing described above, resolution of a strain sensor for strain measurement may be adjusted by changing the initial gauge length (L). For example, if a strain measurement resolution is 10 microstrain, the original gauge length may be designed to be 10 mm. As a result, the required distance measurement resolution will be 100 nm.

Unlike traditional optical fiber strain gauges that use an optical fiber as a sensing element, the sensor herein measures strain as a distance change between an optical fiber and a surface of a target. Consequently, optical fibers described herein are not under strain; any fragility of an optical fiber will not effect sensor reliability or reproducibility. In addition, fatigue life of a strain sensor herein is determined by fatigue resistance of material between the optical fiber sensor and the surface of the target. Hence, a sensor herein may be pre-designed to meet any fatigue resistance requirements.

Because sensors as described herein (e.g., for fatigue/strain/corrosion) are of compact size, they are easy to embed with or in any number of targets (e.g., biologic material, chemical material, industrial material, machine, equipment, transportation/aerospace structure, as examples). Moreover, because of the small size of the optical fiber, one or more pairs of optical fibers may be incorporated into a single package to monitor/detect/identify/predict changes of one or more target materials (or one or more material property changes) by using different portions of the target surface. Statistical calculations based on predictive information may provide future occurrence of corrosion or other material property changes.

Figure 8:
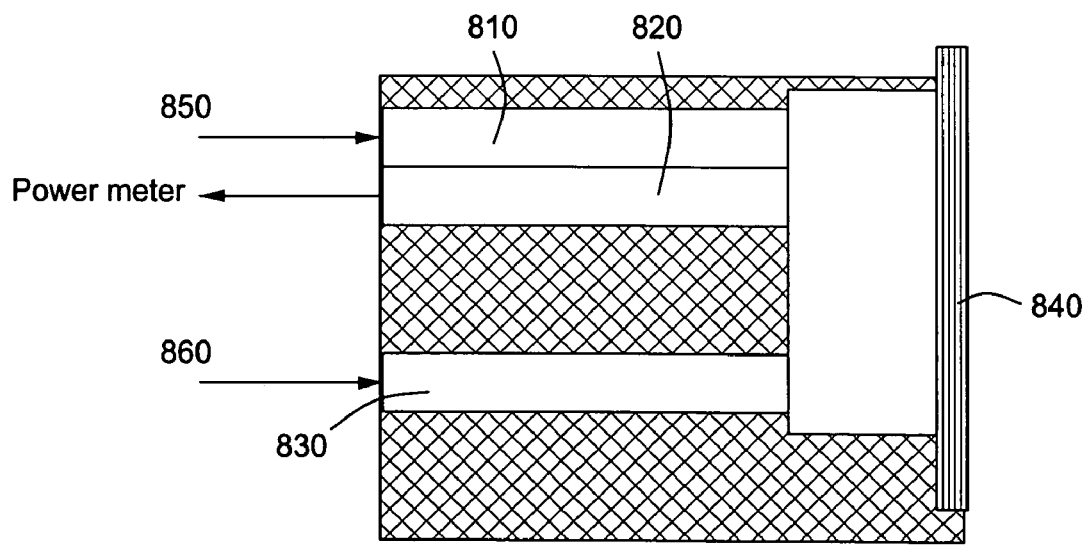
FIG. 8 depicts a schematic of a further sensor design.

In one or more embodiments, the sensor described is a microstructure sensor. Such a sensor may sense surface roughness, plastic deformation, wave speed propagation and attenuation of an ultrasound wave. For plastic deformation, a nonlinear parameter of an ultrasound wave and/or plastic deformation induced surface changes may be assessed. While two separate sensors may be provided, as an alternative or in addition, a single, mutifunctional sensor may be configured as shown in FIG. 8. The property to be detected/assessed/monitored will influence the light source and detector that is coupled to optical fibers of the sensor. The sensor may provide both real-time information (e.g., during operation of the target) and at-a-glance/standardized information about the target and material properties therein.

Referring now to FIG. 8, the sensor comprises at least three parallel optical fibers. Two fibers, fibers 810 and 820 are aligned and adjacent. A third fiber 830 is at a distance from fiber 810 and 820. Fiber 810 is a source fiber that delivers light to target 840.

For sensing of a microstructural feature/property such as surface roughness, a light source 850 is used to direct continuous light via fiber 810 to sensing material target 840. Part of the reflected light from target 840 is collected by fiber 820. A rough surface of the target and/or other structural change (e.g., corrosion pit) will scatter light, resulting in a reduction in intensity of the reflected light. Intensity of the reflected light collected by fiber 820 correlates with the surface roughness/structural change of target 840.

For sensing of wave propagation, a high power short-duration excitation light pulse 860 is delivered to target 840 via fiber 830. Because of a rapid expansion and contraction of the surface of the target being irradiated, surface acoustic waves (SAW) will be generated at the surface of target 840 and propagate from the surface of target 840. The disturbance at the surface generated by SAW will be measured by reflected light which is collected by fiber 820. This is based on a same principle as described previously. Propagation speed of SAW is determined from the delay time between firing of the excitation light 860 and detection of SAW by fiber 820. Attenuation of SAW is determined from the amplitude of SAW from target 840.

For a sensor as described in FIG. 8, a side view of the sensor design is also provided by FIG. 3A. The illuminating fiber 810 is typically a SMF. The receiving fiber 820 is typically an MMF. The core diameter of the SMF is $2a_1$, and the distance d is the distance between the optical fibers and the target. The small circle in the center indicates the core of the SMF while the circle to the right of the SMF indicate the fiber core of the MMF. Accordingly, $w = 2d \tan[\sin^{-1}(NA)] + 2a_1$, where NA is the numerical aperture of the optical fiber.

Because the two fibers 810 and 820 are aligned adjacent to each other, a distance $R_o$ between the centers of the two fiber cores is equal to the diameter of an optical fiber (e.g., 125 microns). Assuming $P_0$ is total power of the reflected light, an intensity profile of the reflected light is assumed to be Gaussian and, $$I(r) = \frac{P_0}{\pi w^2} e^{-r^2/w^2}.$$

Because the intensity profile is axis-symmetric, optical power dP(r) for an overlapping area between the fiber core and a ring with an inner diameter r and an outer diameter r+dr is calculated as $$dP = I(r) 2\beta r dr = \frac{2P_0}{\pi w^2} e^{-r^2/w^2} \cos^{-1}\left(\frac{r^2 + d^2 - a_2^2}{2rd}\right) r dr.$$

The total power of the reflected light that is coupled into the receiving fiber is then calculated by integrating the radius r from $R_0 - a_2$ to $R_0 + a_2$, i.e., $$P = \int_{R_0 - a_2}^{R_0 + a_2} \frac{2P_0}{\pi w^2} e^{-r^2/w^2} \cos^{-1}\left(\frac{r^2 + d^2 - a_2^2}{2rd}\right) r dr. \quad (2)$$

Equation 2 describes a relationship between output optical power of the receiving fiber as a function of the distance between the optical fibers and the target, assuming the surface of the target has a mirror finish. For a rough surface, illumination light is highly scattered. Consequently, the radius of the reflected light pattern increases due to light scattering. Assuming the power of the light source is constant, intensity of the reflected light is reduced with increasing light scattering. Moreover, light scattering may increase the incident angle of the reflected light, which in turn will reduce the output optical power of the receiving fiber, due to its numerical aperture. Both effects change the output power of fiber 820 as surface microstructure (e.g., roughness) of the target changes. Consequently, surface roughness of a target may be monitored by measuring output power of receiving fiber 820.

For acoustic wave excitation, a light source with a modulation repetition rate up to 1 GHz was combined with an optical amplifier (e.g., a doped optical amplifier). The combination provides narrow band excitation of SAW with tunable repetition rate from about 100 KHz to over 30 MHz. For detection of SAW, the distance/acoustic sensor described herein is used. Frequencies from several to tens of megahertz are typically used for detecting/assessing grain size and plastic deformation.

Grain size measurement using ultrasound waves is based on measuring scattering of ultrasonic wave due to grain boundaries and grain orientations. An attenuation coefficient α is related to the mean grain size D and frequency $f$ as shown below: $\alpha = K f^4 D^3$, where K is a constant for a particular material. To reduce uncertainties in grain size measurement, it is preferable to measure the attenuation coefficient α at several different frequencies and calculate the grain size by curve fitting. In addition, in order to measure the nonlinear parameter β of the ultrasound waves due to plastic deformation, narrowband acoustic excitation is employed which can not be achieved by conventional single pulse laser excitation.

Figure 9:
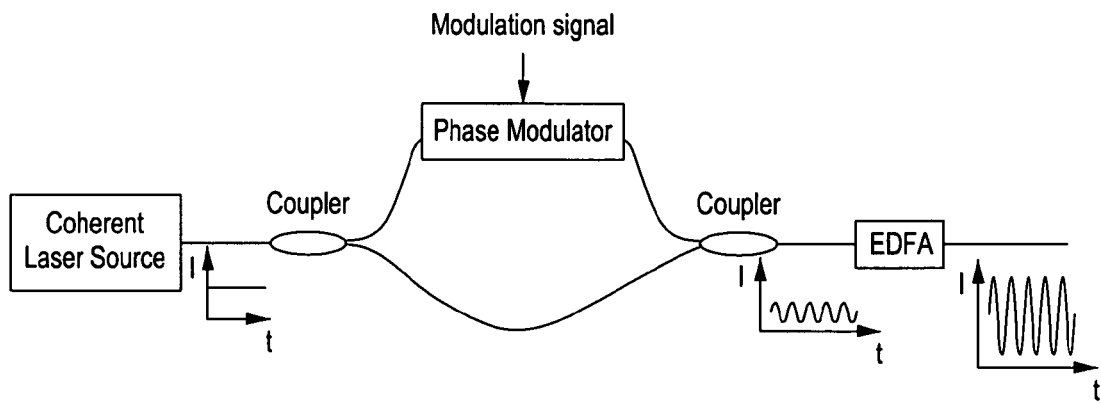
FIG. 9 depicts in schematic form a diagram of a fiber laser described.

For tunable frequency and narrowband ultrasound excitation, a high power optical fiber laser with tunable repetition rate for ultrasound wave generation is used. A schematic of a fiber laser that may be used herein is depicted in FIG. 9. Optical light emitted from a low power continuous wave laser is split into two fibers using a 50/50 fiber coupler. One fiber is directly connected to a second coupler while the other fiber is passed through a phase modulator. When the two optical waves recombine at a second coupler, they interfere (constructively or destructively, depending on phase difference introduced by the phase modulator). Varying the phase of one optical wave continuously produces a sinusoidal optical wave at the output of the second coupler. The period of the sinusoidal wave is controlled by the phase modulation signal; sinusoidal modulations of up to several gigahertz may be used. The optical wave is then amplified with an erbium doped optical fiber amplifier producing a sinusoidal varying optical wave with a high maximum intensity (e.g., greater than 5 watt). Focusing the optical wave that exits the fiber on a portion of the target (e.g., a surface diameter of about 5 micrometer), will excite SAW in many/most materials, including metallic ones.

Figure 10:
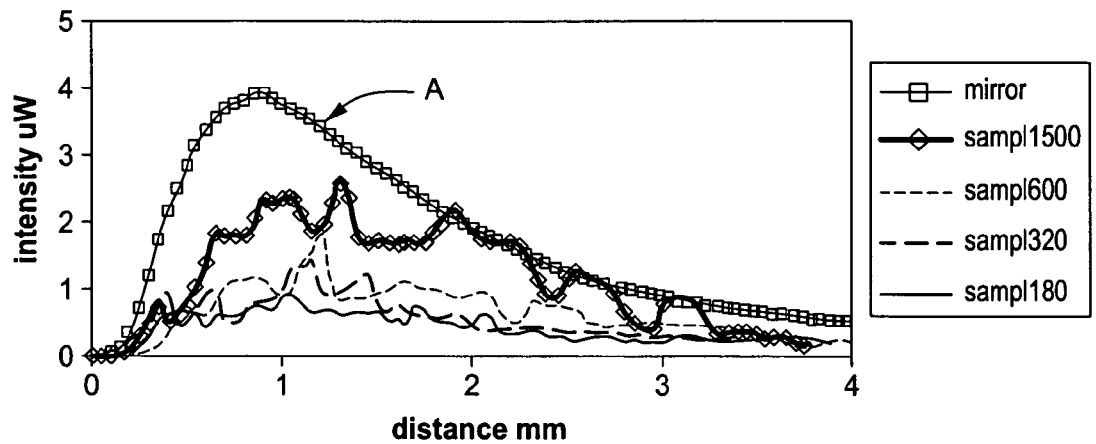
FIG. 10 depicts optical intensity of various samples when assessed by a sensor described.

In a first example, a microstructure sensor as described herein correctly identified changes in surface microstructure of a material using a range of distances between the sensor probe and steel (from 0 to 4 mm). A material was fabricated and samples of the material were then further processed to varying degrees of roughness on one surface by polishing the sample surface using sand paper of grit sizes 180, 320, 600 and 1500. The material was steel. FIG. 10 shows the sensor's ability to detect surface roughness; light intensity of the collected light decreased with increasing surface roughness; surface roughness of the samples was compared to that of a mirror (line A).

Figure 11:
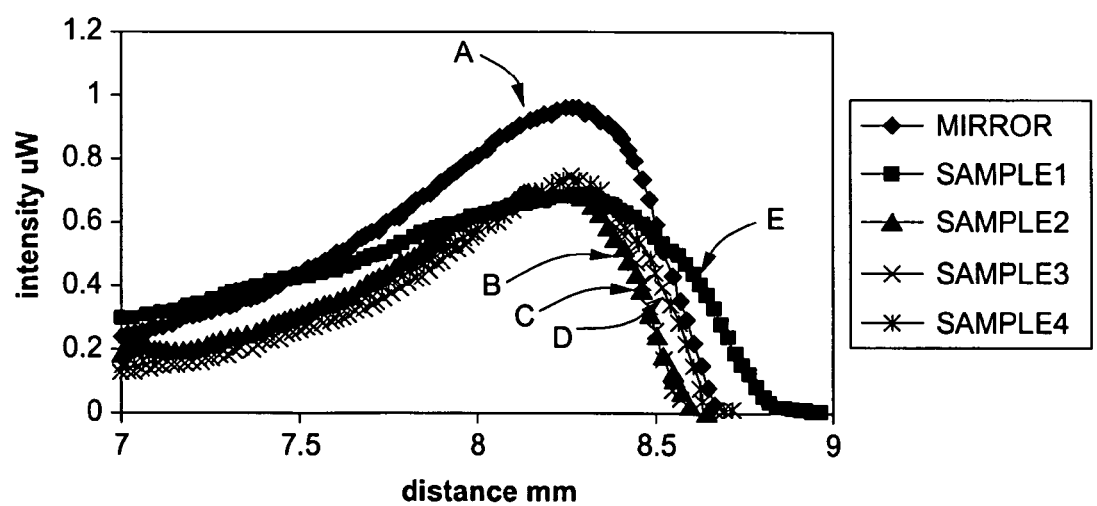
FIG. 11 depicts optical intensity of various samples when assessed by a sensor described.

In another example, a microstructure sensor as described herein correctly identified changes in surface microstructure of a material. A titanium alloy material having a highly polished surface was pre-fabricated and samples were obtained from the material, some of the samples were then further prepared for varying surface microstructures. Three samples had similar surface roughness ($R_q$=about 10-30 nm) and one sample had a larger surface roughness ($R_q$>100 nm). Surface roughness had been measured by a scanning whitelight interferometric microscope (SWLI). When assessed by a sensor provided herein, the distance-intensity relationship for the three smoother samples (lines B, C, D) were similar to that of a mirror (line A). Distance between the sensor probe and steel was from 0 to 4 mm. The distance-intensity relationship of the sample with a larger surface roughness (line E) depicted a broadening of the scattered light, as shown in FIG. 11.

Figure 12A:
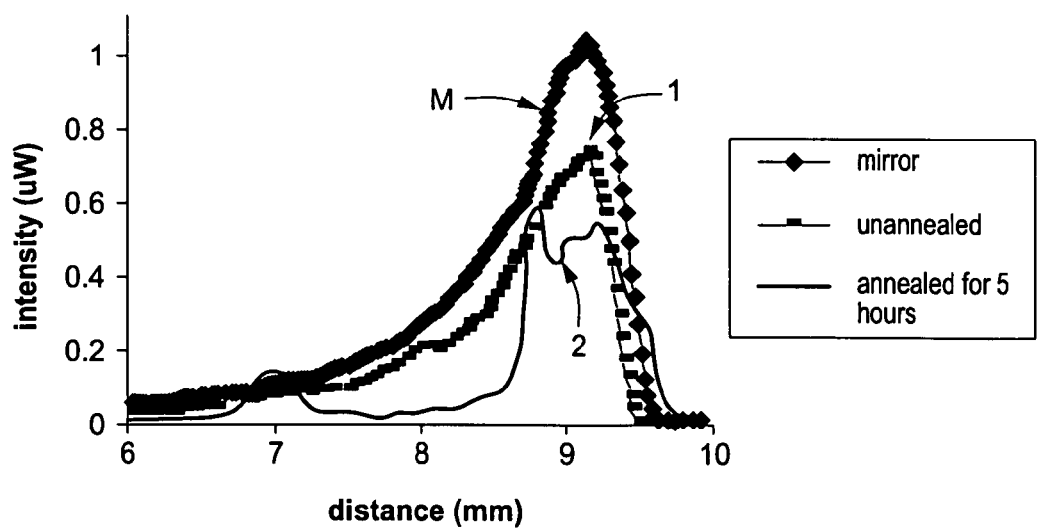
FIG. 12A depicts optical intensity of various samples when assessed by a sensor described.

In still another example, a microstructure sensor as described herein correctly identified changes in surface microstructure of a material. For FIG. 13, one of the smoother samples identified with FIG. 11 (sample D) was annealed at 860 degrees C. for five hours. A sensor assessed surface microstructure of the sample before (line 1) and after (line 2) annealing, and FIG. 12A shows the intensity of the collected light for the samples as compared with that of a mirror (line M). Distance between the sensor probe and steel was from 0 to 4 mm. The intensity curve for the non-annealed sample clearly indicates a smoother surface as compared with a rougher surface after annealing, due, in part, to uneven out-of-plane grain growth with annealing. Optical images of the samples confirm the microstructure changes identified by the sensor, where FIG. 12B is the sample before annealing and FIG. 12C is the sample after annealing.

Figure 13A:
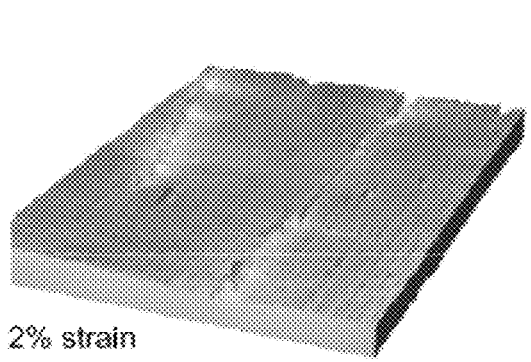
FIGS. 13A and 13B depict three-dimensional (3D) surface profiles of samples after loading at (A) 2% strain and (B) 10% strain.
Figure 13B:
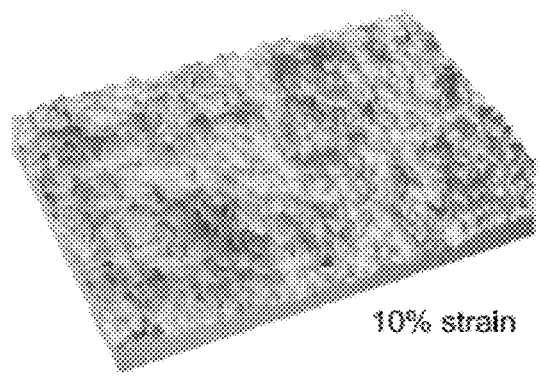
Figure 13C:
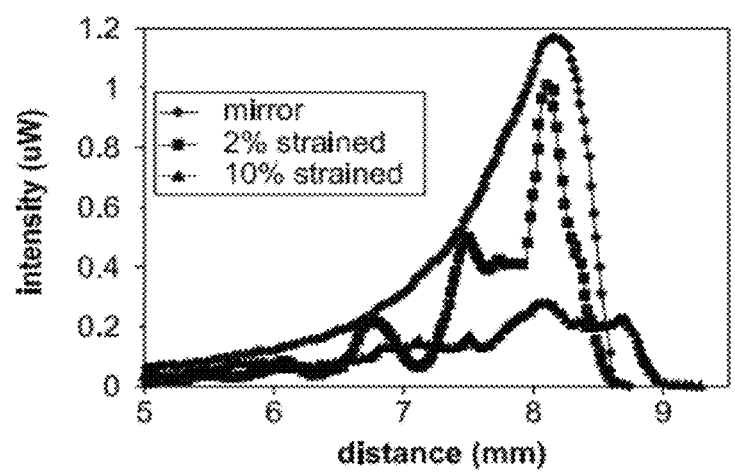
FIG. 13C depicts optical intensity of samples from FIG. 13A when assessed by a sensor described.

In yet another example, a surface roughness sensor as described herein correctly identified plastic deformation of a material. A material of titanium-aluminum metal alloy was prepared into two samples. One sample was loaded to 2% strain and another loaded to 10% strain. The surface roughness of the two samples after loading is provided in the TABLE. Surface roughness was measured by a SWLI. A 3D surface profile image of each sample taken after loading is shown in FIGS. 13A (2% strain) and 13B (10% strain). The two samples after loading where assessed by a deformation sensor as previously described. Distance between the sensor probe and steel was from 0 to 4 mm. The intensity output of the two samples is shown in FIG. 13C. FIG. 13C shows that plastic deformation induced surface roughness changes which increased with an increased loading condition. Consequently, the intensity of the collected light for the 10% strained sample was significantly lower than the 2% strained sample. FIG. 13 indicates that a surface roughness sensor may properly characterize plastic deformation experienced by a material

TABLE

| Strain | $R_q$ (mm) |
|---|---|
| 2% | 72.6 |
| 10% | 206.5 |

In one or more embodiments, described herein is a corrosion sensor. For corrosion sensing, corrosion will typically initiate at the outer surface of a sacrificial film first as depicted with FIG. 1B. As exposure time increases, corrosion pits will grow deeply into the sacrificial film. Should corrosion be deep enough that the pits reach the other side of the sacrificial film, reflectivity of the polished surface (the non-facing surface) will be altered, resulting in a decrease in the output optical power of the sensor. In another word, a corrosion sensor as described herein will typically detect corrosion when such effects are severe enough to penetrate through the thickness of the sacrificial film.

Figure 15:
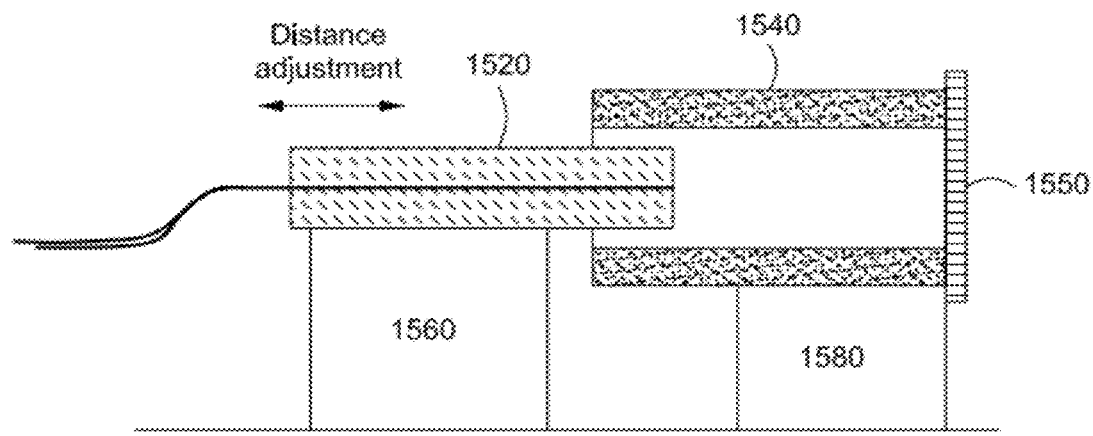
FIG. 15 depicts a further a representative sensor system as described herein.

In a further example, a sensor probe 1520 was constructed by packaging two optical fibers in a 25 mm (1 inch) long stainless steel tube, as depicted in FIG. 15. The tube has an outer diameter of 3 mm (⅛ inch) and an inner diameter of 1.4 mm (0.055 inch). After proper alignment of the two fibers inside the tube, a special optical fiber epoxy was injected into the tube through a syringe and was left for curing. Subsequently, the optical fibers were cleaved using a fiber scriber. The sensor probe 1540 was then inserted into a polishing disk and was polished in a circular FIG. 8 pattern with aluminum oxide polishing films. Polishing included four steps with four polishing films each having a decreasing grit sizes (5 μm, 3 μm, 1 μm and 0.3 μm) that produced a smooth, scratch-free surface for the two fibers.

A coldrolled 1010 steel film with a thickness of 100 μm was selected as the sacrificial material. One side of the steel film was finely polished to maximize light reflection. The polished side of the steel film was then glued to the end of a stainless steel tube 1550 using a waterproof epoxy. This stainless steel tube also served as housing for the sensor head with an outer diameter of 6.4 mm (¼ inch), an inner diameter of 3.9 mm (0.152 inch), and is 12.5 mm (½ inch) in length. It is noted that dimensions described herein, including the outer diameter of the steel tube may be reduced if a smaller size is required or enlarged as desired.

The tube and film subassembly and the sensor probe were assembled together by placing the sensor probe on a three-axis translational stage 1560. The subassembly was aligned using a two-axis rotation stage 1580 so that the sensor probe was perpendicular to the sacrificial film. The distance between the fibers and the sacrificial film was chosen so that the probe operated at the two linear regions of the distance-intensity curve described with FIG. 14 below.

Figure 14:
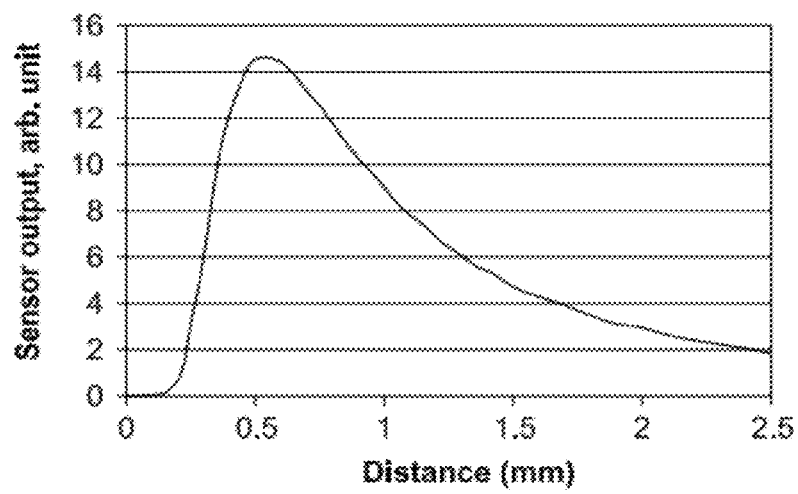
FIG. 14 depicts a representative relationship between sensor output and distance.

At the assembly stage, the inner surface of the sacrificial film has a mirror-finished surface. Therefore, sensor output is determined by the distance between the sensor probe and the sacrificial film. As shown in FIG. 14 (further described in Huang, et al. 2007, presentation at 6$^{th}$ International Workshop on Structural Health Monitoring, Stanford University, Sep. 11-13, 2007, herein incorporated by reference), using a distance vs. power relationship, distance between the sensor probe and the sacrificial film may be precisely adjusted by monitoring sensor output using an optical power meter. Once the distance between the sensor probe and the sacrificial film was adjusted properly, the sensor probe was glued to the tube and film subassembly using a water proof epoxy.

Figure 16:
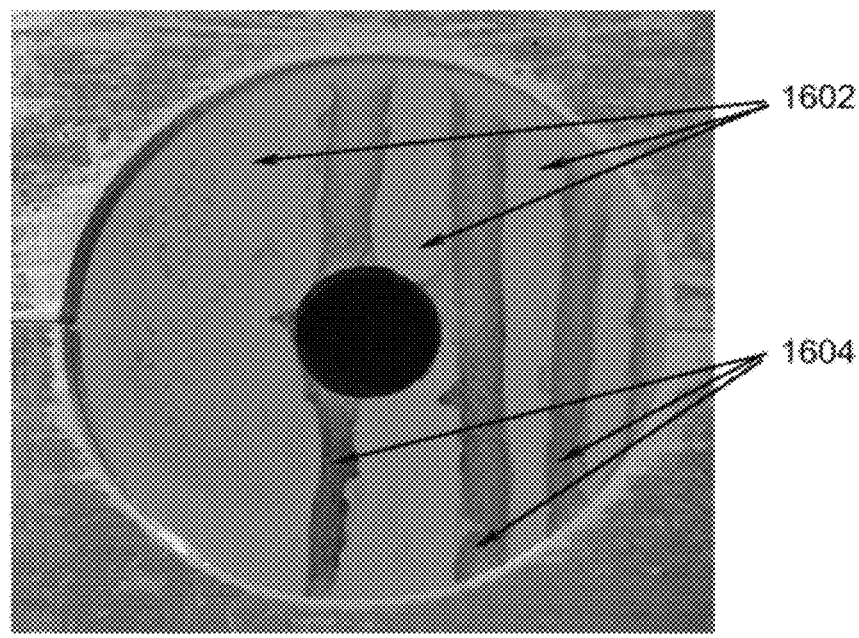
FIG. 16 depicts a representative structure having corroded and uncorroded regions.

Performance of the optical fiber based corrosion sensor described above is shown in FIGS. 17 and 19. In a first example, corroded steel disks as depicted in FIG. 16 were characterized using a sensor probe in a bench top format in which a sensor probe as described with FIG. 15 was mounted on a stationary platform and aligned to be perpendicular to the surface of the steel disk. The SMF of the sensor probe was connected to a 1550 nm, 19.4 mW distributed feedback (DFB) laser source. The MMF of the sensor probe was connected to an optical power meter, which generates a calibrated analog signal that was proportional to the optical power output of the sensor probe. A data acquisition system was programmed to acquire the analog signal into the computer automatically. The corroded steel sample was placed on a three-axis motorized translational stage. The sensor probe was first aligned pointing to an uncorroded region of the steel disk. The distance between the sensor probe and the steel sample was again adjusted based on the distance-power curve of the sensor probe. Once the distance between the sensor probe and the steel disk was fixed, corrosion measurements were performed by traversing the translational stage in a direction that was perpendicular to the corrosion bands. Therefore, alternating bands of corroded and uncorroded surfaces were profiled by the sensor probe. The position of the translation stage and the sensor output were acquired simultaneously, from which the sensor output vs. the positions of the sample were plotted.

After confirming that corrosion development in the steel disks reduced optical power output of the sensor probe, packaged corrosion sensors were fabricated and submerged in saline solution over time to detect the corrosion development in the sacrificial film.

As depicted in FIG. 16, alternating corroded regions 1604 and non-corroded regions 1602 were prepared on the same steel disk. The steel disks were then polished with sand paper to remove superficial corrosion on the surface before measurements were taken.

Figure 17A:
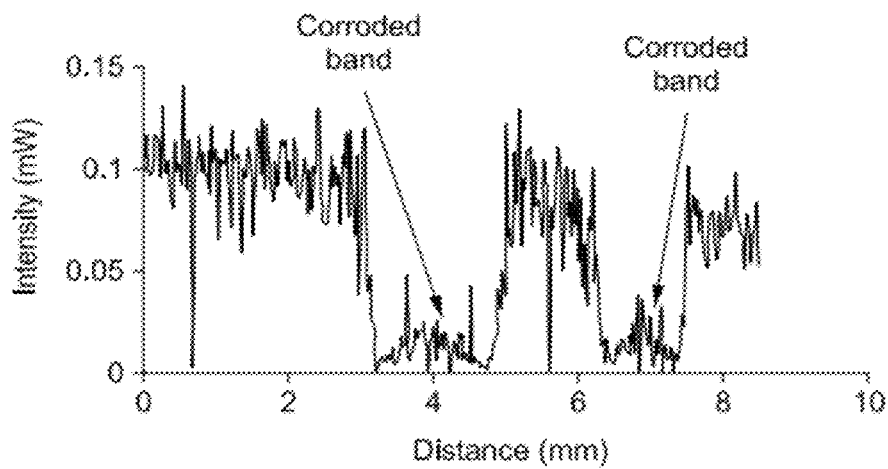
FIG. 17A depicts a representative intensity profile of the structure of FIG. 16.
Figure 17B:
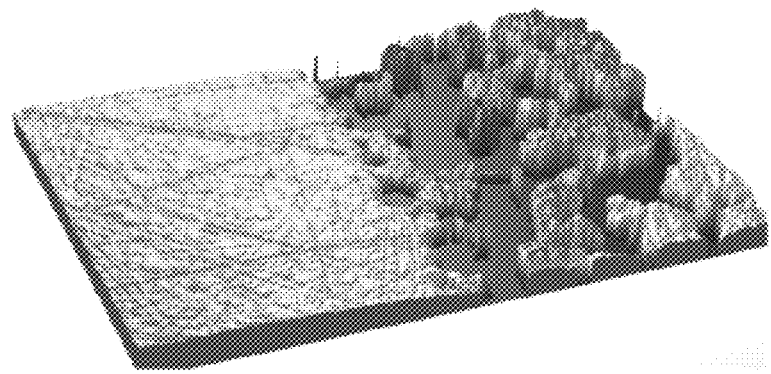
FIG. 17B depicts a representative image in three dimensions showing a corrosion profile as depicted in FIG. 17A.

FIG. 17A shows the bench top measurement and the drop in sensor output when the laser light shines on the corrosion pit; measurements correlated very well with the corrosion bands of the steel disk. FIG. 17B show, in three dimensions, corrosion of such a portion of the steel disk verifying measurements of FIG. 17A.

Figure 18:
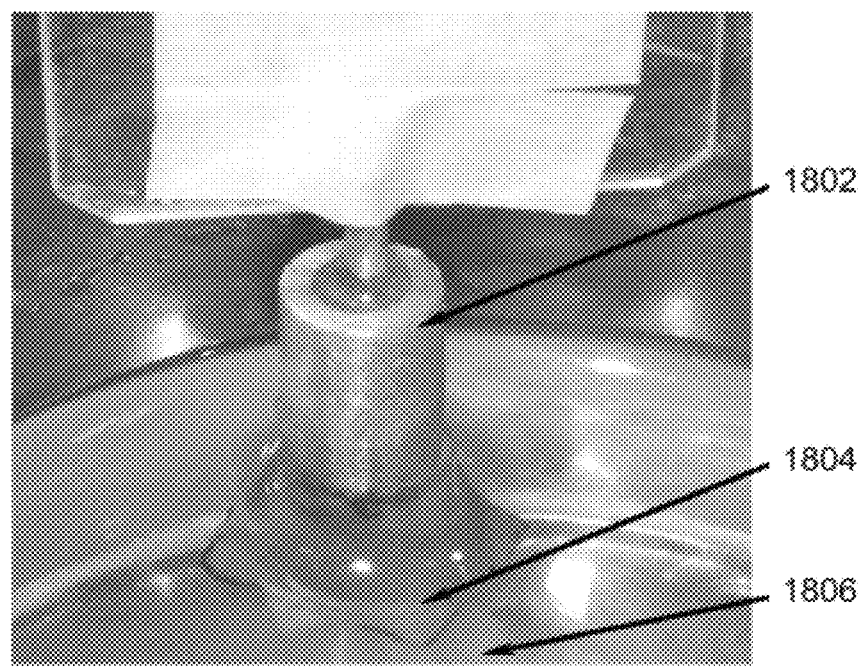
FIG. 18 depicts a sensor fabricated as described herein.
Figure 19:
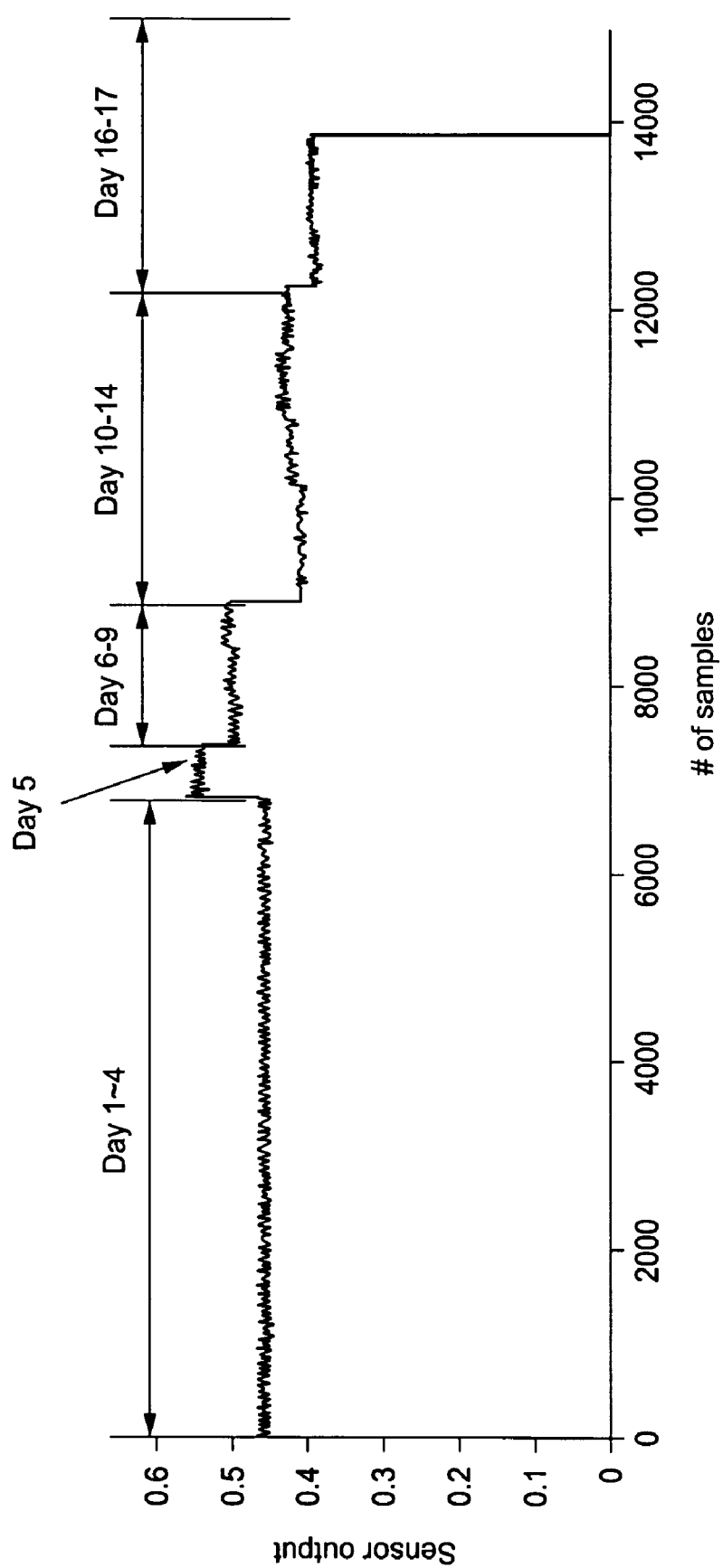
FIG. 19 depicts a representative sensor output over time.

Packaged corrosion sensors with sacrificial steel film attached were tested by submerging them in a saline solution as depicted in FIG. 18, in which sensor head packaged in the stainless steel tube is 1802, the sacrificial film is 1804 and the saline solution is 1806. A laser source illuminated the sensor probe. Output of the sensor probe was measured by a optical power meter on a daily basis. Continuous measurements (over 17 days) were compiled and depicted in FIG. 19. Fluctuation in the line reading between day 5 and days 6-9 and days 10-14 were the result of construction work performed near the apparatus. Overall, sensor output as depicted in FIG. 19 was stable over time. Sensor output dropped drastically between days 16-17 likely due to some water condensation on the polished side of the metallic film. Some corrosion pits were also observed on the surface when the package was disassembled.

Figure 20:
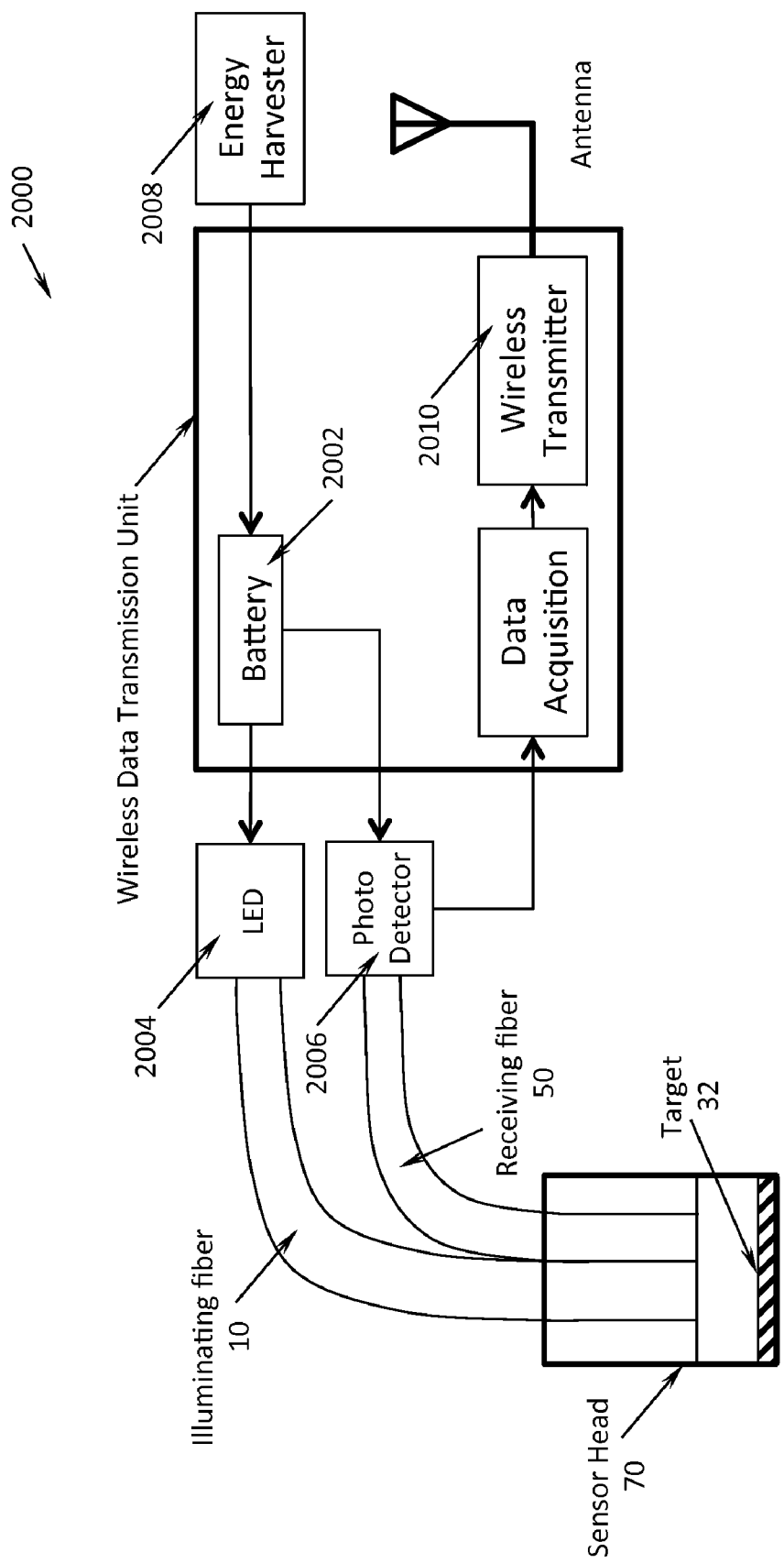
FIG. 20 depicts a block diagram of a battery-operated sensor.

A sensor as described herein may be cooperative with one or more materials. Such a sensor may be provided in a confined space with or without additional optical fibers. Such a sensor may be further cooperative with other equipment, hardware and/or software. In addition as shown in FIG. 20, an optical sensor 2000 may be prepared with a battery 2002 and a battery-operated low power device, such as light emitting diode (LED) 2004 and/or photo-detectors 2006. Furthermore, one or more sensor units described herein, an energy harvesting unit 2008, and a wireless data transmission unit 2010 may be integrated into a small packaged sensor as described herein, which will allow the described sensor to operate in an untethered fashion.

As described herein is a multifunctional sensor relying on light scattering properties of a surface. The sensor is reliable, sensitive, and designed for endurance, especially under sustained loading conditions. The sensor provides direct measurement, assessment, detection, and/or monitoring of a material using optical properties, such as light reflection. The sensor may assess or predict changes in one or more properties and/or be combined with a second sensor to provide an improved approach to measuring, assessing, monitoring, predicting and/or detecting very small changes in a material, its surface or its microstructure, such changes to be assessed as desired, such as over time and under different temperature/operating conditions. Consequently, a sensor described herein is engineered for real time or intermittent usage, which, in part, depends on the material itself and the assessment to be made.

Additional advantages and novel features of the invention as set forth in the description, will be apparent to one skilled in the art after reading the foregoing detailed description or may be learned by practice of the invention. The advantages of that described herein may be realized and attained by means of the instruments and combinations particularly pointed out here.

What is claimed is:

1. A sensor comprising:
    an optical sensor probe comprising at least two optical fibers in parallel;
    a reflective target that is substantially perpendicular to the at least two optical fibers and separated from the at least two optical fibers by a distance; and
    wherein at least one optical fiber is a single mode optical fiber that illuminates a portion of the reflective target, at least one optical fiber is a multi-mode optical fiber collects a reflected light from the reflective target and a change in an optical power output of the collected reflected light is a direct measure of a change in a strain between the optical sensor probe and the reflective target, a deformation between the optical sensor probe and the reflective target, a corrosion, a fatigue or a surface roughness of the reflective target or a material disposed on a surface of the reflective target.

2. The sensor of claim 1, wherein the single mode optical fiber of the at least two optical fibers is coupled to a light source and the multi-mode optical fiber of the at least two optical fibers is coupled to a light detector.

3. The sensor of claim 1, wherein the optical sensor probe includes three parallel optical fibers only one of which delivers light from the reflective target to a detector.

4. The sensor of claim 1, wherein the optical power output is a function of (a) the strain, the deformation, the corrosion, the fatigue or the surface roughness of the reflective target or the material disposed on the reflective target, and (b) the distance between the at least two optical fibers and the reflective target.

5. The sensor of claim 1, wherein the optical sensor probe and the reflective target are packaged into a sensor head that is 10 mm or less in diameter.

6. The sensor of claim 1, wherein the reflective target is a sacrificial material when measuring the change in the corrosion, the fatigue or the surface roughness of the reflective target or the material disposed on the surface of the reflective target.

7. The sensor of claim 1, wherein the distance between the optical sensor probe and the reflective target is between 0.2 mm and 4 mm.

8. A sensor comprising:
    a sensor probe substantially perpendicular to a reflective target and separated by a distance, wherein the sensor probe includes at least a first optical fiber and a second optical fiber, wherein (1) the first optical fiber is a single mode optical fiber that delivers a light to at least a portion of the reflective target to be collected by the second optical fiber which is a multi-mode optical fiber, (2) an optical power output from the second optical fiber is a function of (a) a strain, a deformation, a corrosion, a fatigue or a surface roughness of the reflective target or a material disposed on a surface of the reflective target and (b) the distance between the sensor probe and the reflective target, and (3) a change in the optical power output from the second optical fiber is a direct measure of a change in the strain between the sensor probe and the reflective target, the deformation between the sensor probe and the reflective target, the corrosion, the fatigue or the surface roughness of the reflective target or the material disposed on the surface of the reflective target.

9. The sensor of claim 8, wherein the change in the optical power output comprises:
    a decrease in the optical power output whenever the corrosion, the fatigue or the surface roughness of the reflective target or the material disposed on the surface of the reflective target increases; and
    an increase or decrease in the optical power output whenever the strain or deformation of the reflective target or the material disposed on the surface of the reflective target increases depending on the distance between the optical sensor probe and the reflective target.

10. The sensor of claim 8 further comprising a third optical fiber that delivers light to the reflective target.

11. A sensor assembly comprising
    a sensor probe substantially perpendicular to a reflective target and separated by a distance, wherein the sensor probe includes at least a first optical fiber and a second optical fiber,
    a light source coupled to the first optical fiber which is a single mode optical fiber; and
    a detector coupled to the second optical fiber which is a multi-mode optical fiber, wherein a light from the first optical fiber illuminates at least a portion of the reflective target and is collected by the second optical fiber, wherein (1) an optical power output from the second optical fiber is a function of (a) a strain, a deformation, a corrosion, a fatigue or a surface roughness of the reflective target or a material disposed on a surface of the reflective target and (b) the distance between the sensor probe and the reflective target, and (2) a change in the optical power output from the second optical fiber is a direct measure of a change in the strain between the optical sensor probe and the reflective target, the deformation between the sensor probe and the reflective target, the corrosion, the fatigue or the surface roughness of the reflective target or the material disposed on the surface of the reflective target.

12. The assembly of claim 11, wherein the assembly includes an energy harvesting unit and a wireless data transmission unit.

13. The assembly of claim 11, wherein the light source is a laser light source or a light emitting diode (LED) light source.

14. The assembly of claim 11, wherein the distance between the sensor probe and reflective target is chosen for the sensor assembly to operate at a linear region of a distance-intensity curve.

15. The assembly of claim 11, wherein the sensor probe and the reflective target are packaged into a sensor head having a diameter of 10 mm or less.

16. The assembly of claim 11, wherein the reflective target is metal.

17. The assembly of claim 11, wherein the distance between the sensor probe and the reflective target is between 0.2 mm and 4 mm.

18. A method of sensing comprising the steps of:
providing a sensor probe substantially perpendicular to a reflective target and separated by a distance, wherein the sensor probe includes at least a first optical fiber and a second optical fiber,
illuminating at least a portion of the reflective target through the first optical fiber which is a single mode optical fiber; and
collecting the reflected light through the second optical fiber which is a multi-mode optical fiber, wherein (1) an optical power output from the second optical fiber is a function of (a) a strain, a deformation, a corrosion, a fatigue or a surface roughness of the reflective target or a material disposed on a surface of the reflective target, and (b) the distance between the sensor probe and the reflective target or the material disposed on the surface of the reflective target, and (2) a change in the optical power output from the second optical fiber is a direct measure of a change in the strain between the optical sensor probe and the reflective target, the deformation between the sensor probe and the reflective target, the corrosion, the fatigue or the surface roughness of the reflective target or the material disposed on the surface of the reflective target.

* * * * *